United States Patent [19]

Mitsuhata et al.

[11] 4,248,740

[45] Feb. 3, 1981

[54] PROCESS FOR PREPARING SILVER-SUPPORTED CATALYST FOR THE PRODUCTION OF ETHYLENE OXIDE

[75] Inventors: Masashi Mitsuhata; Toshihiko Kumazawa, both of Yokohama; Isamu Kiguchi, Zushi, all of Japan

[73] Assignee: Nippon Shokubai Kagaku Kogyo Co. Ltd., Osaka, Japan

[21] Appl. No.: 920,117

[22] Filed: Jun. 28, 1978

[30] Foreign Application Priority Data

Jul. 1, 1977 [JP] Japan ................................. 52-77752

[51] Int. Cl.³ .......................................... B01J 23/48
[52] U.S. Cl. ................................. 252/463; 252/476; 260/348.34
[58] Field of Search ................ 252/463, 476; 427/243; 260/348.34

[56] References Cited

U.S. PATENT DOCUMENTS 4,033,903  7/1977  Maxwell .............................. 252/476

FOREIGN PATENT DOCUMENTS 46-19606 of 1971 Japan ......................................... 252/476
1451870 10/1976 United Kingdom ..................... 427/243

Primary Examiner—Evan K. Lawrence
Attorney, Agent, or Firm—Sherman & Shalloway

[57] ABSTRACT

An improved process for preparing a silver-supported catalyst for use in the production of ethylene oxide by catalytic vapor phase oxidation of ethylene with molecular oxygen, which comprises impregnating a porous inorganic carrier with a solution of a silver compound containing a reducing compound, subjecting the impregnated product to a reducing treatment at 50° to 200° C. to disperse and deposit metallic silver on the external surface of the carrier and the internal surfaces of its pores, washing the silver-supported carrier with water, a lower alcohol or both, drying the washed product at a temperature of 50° to 150° C., impregnating the dried product with a solution containing a promoter, and evaporating the liquid ingredients.

9 Claims, No Drawings

PROCESS FOR PREPARING SILVER-SUPPORTED CATALYST FOR THE PRODUCTION OF ETHYLENE OXIDE

BACKGROUND OF THE INVENTION

This invention relates to a process for preparing a silver-supported catalyst for the production of ethylene oxide. More specifically, it relates to a process for preparing a silver-supported catalyst which when used in the catalytic vapor phase oxidation of ethylene with a molecular oxygen-containing gas, can afford ethylene oxide with a high level of catalytic activity.

Catalysts for use in the commercial production of ethylene oxide by catalytic vapor phase oxidation with molecular oxygen are required to have a long catalytic lifetime in addition to a high activity and selectivity. Many silver-supported catalysts have been suggested heretofore in an attempt to improve these properties. For example, the inventions disclosed in British Pat. Nos. 1,300,971, 1,020,759, and 1,413,251, U.S. Pat. No. 3,702,259, and British Pat. No. 1,489,335 are known. These patent documents disclose that a silver-supported catalyst is prepared by depositing silver or a silver compound together with an alkali metal compound, an alkaline earth metal compound or another metal compound as a promoter on a suitable inorganic carrier by a coating method or impregnating method, and then reducing or heat-treating the product. Such known catalysts attain industrially required levels of conversion of ethylene and selectivity to ethylene oxide, but are still not satisfactory and require further improvement with regard to the method of supporting silver or a silver compound, the selection of the promoter, the method of adding the promoter, the selection of the carrier, and the method of activating the catalyst. For example, the catalytic activity of supported metallic silver is greatly affected by the method of preparing metallic silver, the method of its supporting, the method of activation, etc. The reducing treatment and heat-treatment at a temperature of 250° C. or higher and at times more than 300° C. which are suggested in these documents as improved methods never give stable highly active silver, and moreover involve a danger of explosion and combustion. The type of the promoter compound, the time of its addition and the method of its addition markedly affect the activity of the resulting catalyst. Further, the properties of the carrier, i.e. the specific surface area, the pore distribution, etc. greatly affect the activity or selectivity of the catalyst.

It is an object of this invention therefore to remedy these defects of the prior art in silver-supported catalysts.

SUMMARY OF THE INVENTION

According to this invention, there is provided an improved process for preparing a silver-supported catalyst for use in the production of ethylene oxide by catalytic vapor phase oxidation of ethylene with molecular oxygen, the catalyst being composed of a porous inorganic carrier and fine particles of silver deposited on its external surface and the internal wall surfaces of its pores, which comprises impregnating the porous inorganic carrier with a solution of a silver compound containing a reducing compound, subjecting the impregnated product to a reducing treatment at a temperature of 50° to 200° C. to deposit metallic silver on the external surface of the carrier and the internal surfaces of its pores, washing the silver-supported carrier with water, a lower alcohol or both, drying it, impregnating the dried product with a solution containing a promoter, and then evaporating the liquid ingredients.

The process of the invention brings about various advantages. Firstly, a catalyst is obtained in which very finely divided particles of active silver are well dispersed and firmly adhered to the external and internal surfaces of the carrier. Secondly, a catalyst can be prepared which is safer and more economical than catalysts of this kind suggested heretofore. Thirdly, a drastic decrease in the amount of supported silver, which is impossible with conventional commercial silver-supported catalysts, can now be achieved. Fourthly, the catalyst obtained has a higher activity, a higher selectivity and a longer catalytic lifetime than the conventional catalysts of this kind.

DESCRIPTION OF THE PREFERRED EMBODIMENTS

As is well known, in a silver-supported catalyst for the production of ethylene oxide, the particle size and particle size distribution of silver in the catalyst greatly affect the activity, selectivity and life of the catalyst. Hence, these factors should be carefully considered in the production of the catalyst. The size and size distribution of the silver particles are affected not only by the specific surface area and pore distribution, etc. of the porous inorganic carrier used, but also by the method of depositing active silver on the external and internal surfaces of the carrier. To obtain a catalyst having a high activity, a high selectivity and a long catalytic lifetime in accordance with this invention, the diameter of the silver particles to be deposited on the surface of the carrier should be far smaller than those of conventional commercial catalysts. The particle diameter of silver in catalysts prepared by conventional methods is at least about 2,000 A on an average, whereas the particle diameter of silver in the catalyst of this invention is about 1,000 A or less.

In order to deposit such fine silver particles, heat-treatment at a high temperature exceeding 200° C. as is done in conventional methods should be avoided in the catalyst preparing process of this invention. One method which meets this requirement is the one disclosed in Japanese Patent Publication No. 19606/71 which comprises impregnating a porous inorganic carrier with a solution of a silver compound containing a reducing agent such as ethanolamine, and reducing the impregnated material at a temperature of not more than 200° C. to deposit metallic silver on the carrier. Other known methods of reduction at low temperatures can also be applied to the process of this invention, but heating which is performed in most of these known methods to remove impurities and the organic or inorganic medium after depositing silver metallic silver should be avoided in the present invention. Such heating would give rise to a growth of very fine silver particles deposited by the low-temperature reduction. Accordingly, washing with water as described in the above-cited Japanese Patent Publication No. 19606/71 is preferred as the method of removing impurities and the used medium after the reduction. Washing with a lower alcohol such as methanol or ethanol instead of water is of course possible. The removal of the impurities and the used medium by washing with water not only produces an effect of obtaining fine silver particles, but also serves to activate silver. This also has an important bearing on the addition of a promoter which is the essence of the present invention.

That the catalyst obtained by the process of this invention exhibits a higher activity and a higher selectivity than heretofore attainable is due principally to the improvement of the step of adding the promoter.

The step of adding the promoter in the present invention is significant as a step following the low-temperature reducing step, the water washing step and the drying step. If this sequence is changed, the promoter adding step is quite insignificant. In other words, if the conditions of the present invention are not applied with regard to the method of adding the promoter and the time of its addition, the intended effect is drastically reduced or is not obtained at all. This makes a good contrast with the fact that most of the conventional methods of catalyst preparation give no particular consideration to the time of adding the promoter, or select different times from that chosen by the present invention.

For example, British Patent Specification No. 1,413,251 states that a catalyst having a selectivity of 75 to 81% can be obtained by a method which comprises depositing at least one ion of K, Rb and Cs on a carrier in an amount of 0.00035-0.0030 gram equivalent/kg of catalyst coincidently with deposited silver. One specific working example of this patent states that the deposition of the metal element after the deposition of silver is disadvantageous. U.S. Pat. No. 4,033,903 discloses that at least one ion of K, Cs and Rb is deposited in an amount of 0.00004-0.0008 gram equivalent/kg of catalyst on a catalyst obtained by depositing silver on a carrier and then heat-treating it at 150° to 900° C. to stabilize it. German Pat. No. 2519599 discloses a method which involves impregnating a tired catalyst with Cs and/or Rb in the form of an alcohol solution or an aqueous alcohol solution, and then evaporating the liquid ingredients to deposit 1 to 1000 ppm of Cs and/or Rb based on the catalyst.

In contrast, the process of this invention comprises, in sequence, a step of depositing metallic silver, a step of washing the silver-supported catalyst, a step of drying it, a step of impregnating the dried product with a solution containing a promoter, and then a step of drying the impregnated product to deposit the promoter.

The differences between the process of this invention and the conventional methods will be clearly seen from Comparative Examples to be given hereinbelow, and even when equivalent promoters are used, a great difference in effect will arise between them.

The present invention will now be described in more detail, and the other characteristic features of the invention will become apparent from the detail description.

The catalyst in accordance with this invention is prepared generally by the following procedure.

The solution of a silver compound containing a reducing compound used in this invention may be any of known solutions. For example, a solution of an alkanolamine as the reducing compound and a silver compound dissolved together with water, a solution of formaldehyde as the reducing compound and silver nitrate dissolved together with water, and a solution of a lower acid amide as the reducing compound and silver nitrate dissolved in monoethylene glycol can be advantageously used.

Examples of the alkanolamine are mono-, di- and tri-ethanolamines, mono-, di- and tri-n-propanolamines, mono-, di- and tri-isopropanolamines, n-butanolamines, and isobutanolamines. The lower acid amide includes, for example, formamide, acetamide, propionamide, hydroxyacetamide, and dimethyl formamide. These reducing compounds have a reducing action at room temperature to 200° C. and reduce the dissolved silver compound to metallic silver.

The starting silver compound may be any inorganic or organic silver salt which forms a water-soluble salt by reaction with the alkanolamine. Suitable silver compounds are silver nitrate, silver carbonate, silver sulfate, silver acetate, silver lactate, silver succinate, silver oxalate, and silver glycolate.

Water is a suitable solvent, but lower aliphatic compounds having 2 to 6 carbon atoms and containing 1 to 3 alcoholic hydroxyl groups per molecule are also suitably used when the reducing compound is the lower acid amide. Examples of the lower aliphatic compounds are mono-, di- or tri-ethylene glycols, trimethylene glycol, monopropylene glycol, methyl cellosolve, ethyl cellosolve, methyl carbitol, ethyl carbitol, and glycerol.

The porous inorganic carrier used in this invention may be any known conventional carriers. Carriers composed of alumina and/or silica are preferred. The use of carriers having a high α-alumina content produces especially good results. From the viewpoint of properties, carriers having a specific surface area of not more than 10 $m^2/g$, especially 0.01 to 1 $m^2/g$, an apparent porosity of 40 to 60% by volume and a pore volume of 0.1 to 0.5 cc/g are preferably employed. From the standpoint of the pore size of carrier, carriers having a double pore structure composed of pores with a relatively small diameter and pores with a relatively large diameter are preferred. Such carriers of the double pore structure are disclosed in Japanese Laid-Open Patent Publication No. 20079/72.

Useful promoters in the present invention include many of conventional promoters known in the production of catalytically active materials. Examples are alkali metal compounds, alkaline earth metal compounds, and compounds of elements of groups III, IV, V and VIII of the periodic table. Preferred promoters are compounds of barium, tin, antimony, thallium, potassium and cesium disclosed, for example, in British Pat. No. 1,451,870. They can be used either alone or as mixtures. The amount of metal added is 0.00001 to 0.01 gram-atom as metal per gram-atom of metallic silver in the catalyst.

Especially preferred promoters and their amounts (the amounts of metal per gram-atom of metallic silver in the catalyst) are listed below.

(1) A thallium compound in an amount of 0.00001 to 0.005, preferably 0.00005 to 0.003, gram-atom as thallium.

(2) A mixture of 0.00001 to 0.005, preferably 0.00005 to 0.003, gram-atom as thallium of a thallium compound and 0.00001 to 0.01, preferably 0.0003 to 0.006 gram-atom, as antimony of an antimony compound and/or 0.00001 to 0.01, preferably 0.0003 to 0.006, gram-atom as tin of a tin compound.

(3) A mixture of 0.00001 to 0.005, preferably 0.00005 to 0.003, gram-atom as thallium of a thallium compound and 0.00001 to 0.01, preferably 0.0005 to 0.006 gram atom as potassium of a potassium compound and/or 0.00001 to 0.008, preferably 0.00002 to 0.005, gram-atom as cesium of a cesium compound.

(4) A mixture of 0.00001 to 0.005, preferably 0.00005 to 0.002, gram atom as thallium of a thallium compound, 0.00001 to 0.01, preferably 0.0003 to 0.003, gram atom as antimony of an antimony compound and/or 0.00001 to 0.01, preferably 0.0003 to 0.003, gram-atom as tin of a tin compound, 0.00001 to 0.01, preferably 0.0005 to 0.005, gram-atom as potassium of a potassium compound and/or 0.00001 to 0.008, preferably 0.0002 to 0.005, gram-atom as cesium of a cesium compound.

The promoter is used in the form of a compound soluble in water or a lower alcohol such as methanol, ethanol or propanol, for example in the form of an inorganic compound such as a hydroxide, nitrate, sulfate or carbonate, or an organic compound such as an acetate salt.

The present invention is described more specifically in accordance with one preferred embodiment.

When silver nitrate is dissolved in 0.5 to 5 times its weight of water and 0.8 to 2 times its weight of monoethanolamine is added dropwise with cooling, the silver nitrate is converted to a complex salt through the stage of silver oxide and forms a colorless solution. The solution is impregnated in 3 to 10 times its weight of an α-alumina carrier, and heated at 50° to 200° C., preferably 60° to 150° C. Good results are obtained when this heating is started at a low temperature and the temperature is gradually raised. The heating time is 2 to 12 hours, preferably 4 to 8 hours. The carrier in which active silver is thus dispersed and adhered to the external surface of the carrier and the internal wall surfaces of its pores is then washed with water, preferably with boiling water. This washing removes organic materials such as alkanolamines and cleanses the surface of active silver to render its activity still higher. After washing, the product is dried at a temperature of 50° to 150° C. The dried product is impregnated with a solution of a predetermined amount of a promoter in water or a lower alcohol such as methanol or ethanol or a mixture of water and a lower alcohol. The solvent is then evaporated at 50° to 150° C. In these steps, care should be taken not to heat the catalyst to above 200° C.

When the promoter is impregnated as an aqueous solution, the use of degassed water is preferred. Preferably, the promoter is used in an atmosphere of an inert gas such as nitrogen whether it is in the form of an aqueous solution or a lower alcohol solution. However, as will be clear from Examples to be given hereinbelow, no great difference arises even when it is used in the air.

Other methods of supporting active silver particles are also effective, and good results are obtained even when a lower acid amide is used as the reducing compound. For example, a catalyst having very fine silver particles supported thereon can be prepared by dissolving silver nitrate in 1 to 20 times, especially 1 to 10 times, its weight of a solvent such as ethylene glycol, adding 0.5 to 5 moles, especially 1 to 3 moles, per mole of the silver component, of a reducing compound such as formamide to the resulting solution, impregnating a predetermined amount of a carrier with the resulting solution, heating the impregnated product at 100° to 150° C. for 1 to 10 hours to support silver on the carrier, thereafter washing the silver-supported carrier with water or a lower alcohol and then depositing a promoter in the same way as described hereinabove.

The resulting silver-supported catalyst surprisingly exhibits high levels of performance even when the amount of silver supported is far smaller than those of the conventional known catalysts. The catalyst of this invention shows sufficient activity when the amount of silver supported is 0.5 to 15% by weight, preferably 0.5 to 10% by weight, based on the total weight of the catalyst. Characteristically, even when the amount of silver supported is as small as 1 to 5% by weight, the catalyst exhibit a high level of catalytic activity feasible for commercial application. This is because the catalyst prepared by the process of this invention has relatively fine particles of metallic silver supported on it, and even when the amount of silver supported is small, the specific surface area of the catalyst is higher than in catalysts having large amounts of silver deposited as in the conventional techniques.

As a result of the decrease of the amount of silver supported, the catalyst in accordance with this invention is cheap, and its deterioration caused by the sintering of silver particles which cannot be avoided during use in catalytic reactions is very much reduced. Accordingly, the catalyst of the invention has the advantage of a long catalytic lifetime.

Ethylene is oxidized by using the catalyst of this invention at a reaction temperature of 150° to 300° C., preferably 180° to 250° C., and a reaction pressure of 2 to 40 kg/cm$^2$.G, preferably 10 to 30 kg/cm$^2$.G, at a space velocity of 3,000 to 10,000 hr$^{-1}$ (STP), preferably 5,000 to 8,500 hr$^{-1}$ (STP). The feed gas to be passed over the catalyst contains 0.5 to 30% by volume of ethylene, 3 to 10% by volume of oxygen and 5 to 30% by volume of carbon dioxide and the remainder consisting of an inert gas such as argon, nitrogen or steam and optionally lower hydrocarbons such as methane or ethane. Good results will be obtained if a halogen-containing compound such as ethylene dichloride or diphenyl chloride is added to the feed gas as a reaction inhibitor in an amount of 0.1 to 10 ppm by volume.

Air, pure oxygen and enriched air are examples of a source of molecular oxygen used in this invention.

The following Examples and Comparative Examples illustrate the present invention in more detail. The invention, however, is not limited to these examples so long as it does not depart from the spirit and scope as herein described.

The conversion and selectivity described in this application are defined as follows:

$$\text{Conversion}(\%) = \frac{\text{Moles of ethylene converted}}{\text{Moles of ethylene in the feed gas}} \times 100$$

$$\text{Selectivity}(\%) = \frac{\text{Moles of ethylene converted to ethylene oxide}}{\text{Moles of ethylene converted}} \times 100$$

EXAMPLE 1

Silver nitrate (75 g) was dissolved in 220 g of water, and with cooling over a water bath, 75 g of ethanolamine was added dropwise. The silver nitrate formed a complex salt through the stage of light brown silver oxide precipitated. Thus, a colorless aqueous solution of the complex silver salt was obtained. The solution was impregnated in 1 liter of a spherical α-alumina carrier having a particle diameter of 4 to 6 mm, an apparent porosity of 51 to 55%, a specific surface area, measured by the BET method, of 0.3 m$^2$/g, and a pore volume of 0.28 cc/g with pores having a pore diameter of 0.1 to 5μ accounting for 45% of the total pore volume and pores having a pore diameter of 10 to 20μ accounting for 47% of the total pore volume. The impregnated product was gradually heated to 90° C., stirred at this temperature for 3 hours, heated to 150° C., and further stirred for 2 hours to disperse and deposit reduced silver on the carrier. The resulting silver-deposited catalyst was washed five times with 700 ml of boiling water, and dried at 90° to 100° C. for 5 hours. Then, the dried catalyst was impregnated in an atmosphere of nitrogen with a mixed aqueous solution consisting of 1 ml of a 5% by weight aqueous solution of antimony lactate, 10 ml of a 2.2% by weight aqueous solution of thallium sulfate and 300 ml of water, and then dried in the manner described above.

The catalyst obtained contained 4.5% by weight of silver and about 0.00003 gram-atom per gram-atom of silver of antimony, and about 0.002 gram-atom per gram-atom of silver, of thallium.

The catalyst was packed into a stainless steel reaction tube having an inside diameter of 18.5 mm and a length of 5,000 mm, and while the reaction tube was externally heated gradually from 150° C. with a heat transfer medium, Dowtherm A, a feed gaseous mixture consisting of 20% by volume of ethylene, 8% by volume of oxygen, 7% by volume of carbon dioxide, 1 ppm of ethylene dichloride and the remainder being an inert gas such as nitrogen, methane, ethane or argon was introduced into the catalyst layer and was reacted at a temperature (the temperature of the heat transfer medium) of 211° C. The results obtained by continuing the reaction for 240 hours are shown in Table 1.

EXAMPLE 2

Silver nitrate (75 g) was dissolved in 270 g of monoethylene glycol, and 30 g of formamide was added. The mixture was well stirred, and impregnated in 1 liter of the same carrier as used in Example 1. The impregnated carrier was heated to 130° C., stirred for 2 hours, further heated to 160° C., and stirred for another two hours, and cooled. The resulting silver-supported catalyst was washed five times with 600 ml of boiling water, and dried at 100° C. for 5 hours. The resulting dried catalyst was impregnated with a mixed aqueous solution consisting of 1 ml of a 5.0% by weight aqueous solution of antimony lactate, 10 ml of a 2.2% by weight aqueous solution of thallium sulfate, and 300 ml of water, and dried in the same way as described in Example 1.

The resulting catalyst contained 4.3% by weight of metallic silver, about 0.0003 gram-atom per gram-atom of silver, of antimony, and about 0.002 gram-atom per gram-atom of silver, of thallium supported on it.

The catalyst was packed into a stainless steel reaction tube having an inside diameter of 18.5 mm and a length of 5,000 mm, and while the reaction tube was externally heated gradually from 150° C., a feed gaseous mixture having the same composition as in Example 1 was introduced and was reacted at 213° C. (the temperature of the heat transfer medium) and a pressure of 23 kg/cm².G. The results obtained by continuing the reaction for 240 hours are shown in Table 1.

Comparative Example 1

A catalyst was prepared in the same way as in Example 1 except that 1 ml of a 5% by weight aqueous solution of antimony lactate and 10 ml of a 2.2% by weight aqueous solution of thallium sulfate were added to an aqueous solution of silver nitrate-ethanolamine complex salt, and the step of impregnating the dried silver-supported carrier with a mixed aqueous solution consisting of 1 ml of a 5% by weight aqueous solution of antimony lactate, a 2.2% by weight aqueous solution of thallium sulfate and 300 ml of water was not performed. Specifically, the procedure was as follows:

Silver nitrate (75 g) was dissolved in 220 g of water, and with cooling over a water bath, 75 g of ethanolamine was added dropwise to form an aqueous solution of a silver nitrate-ethanolamine complex salt. Then, 1 ml of a 5% by weight aqueous solution of antimony lactate and 10 ml of a 2.2% by weight aqueous solution of thallium sulfate were added. The resulting aqueous solution was impregnated with the same carrier as used in Example 1. The impregnated product was gradually heated to 90° C., stirred at this temperature for 3 hours, heated to 150° C., and stirred further for 2 hours thereby to disperse and deposit reduced silver on the carrier together with the antimony and thallium ingredients. The resulting supported catalyst was washed five times with 700 ml of boiling water, and dried at 90° to 100° C. for 5 hours.

By using this catalyst, the same reaction as in Example 1 was performed. The results are shown in Table 1.

Comparative Example 2

A silver-supported catalyst obtained by impregnating a carrier with an aqueous solution of a silver nitrate-ethanolamine complex salt and then stirring the impregnated product under heat in the same was as in Example 1 was not subjected to the water washing as in Example 1, but was packed as such into a stainless steel reaction tube having an inside diameter of 18.5 mm and a length of 5,000 mm. While the reaction tube was externally heated to 240° C. by means of a heat transfer medium, Dowtherm A, air was introduced into the catalyst layer for 20 hours to decompose organic and inorganic ingredients remaining in the catalyst. The catalyst was then withdrawn from the reaction tube, and in the same way as in Example 1, impregnated with a mixed aqueous solution consisting of 1 ml, of a 5.0% by weight aqueous solution of antimony lactate, 10 ml of a 2.2% by weight aqueous solution of thallium sulfate and 300 ml of water in an atmosphere of nitrogen, and dried at 90° to 100° C. for 5 hours.

The catalyst so obtained was reacted in the same way as in Example 1. The results are shown in Table 1.

Comparative Example 3

In the same way as in Example 1, a carrier was impregnated with an aqueous solution of a silver nitrate-ethanolamine complex salt, and the impregnated carrier was stirred under heat. The resulting silver-supported catalyst was washed several times with 700 ml of boiling water, and dried at 90° to 100° C. for 5 hours. The catalyst was packed into a stainless steel reaction tube having an inside diameter of 18.5 mm and a length of 5,000 mm, and the reaction tube was externally heated to 240° C. by a heat transfer medium (Dowtherm A). Air was introduced into the catalyst layer for 20 hours. The catalyst was then taken out of the reaction tube, and in the same way as in Example 1, was impregnated with a mixed aqueous solution consisting of 1 ml of a 5.0% by weight aqueous solution of antimony lactate, 10 ml of a 2.2% by weight aqueous solution of thallium sulfate, and 300 ml of water, followed by drying.

By using the resulting catalyst, the same reaction as in Example 1 was performed. The results obtained are shown in Table 1.

Table 1

| Example (Ex.) or Comparative Example (CEx.) | Silver compound | Reducing compound | Reaction temperature (°C.) | Results Conversion (%) | Selectivity (%) |
|---|---|---|---|---|---|
| Ex. 1 | AgNO$_3$ | Monoethanolamine | 211 | 8.0 | 83.1 |
| Ex. 2 | AgNO$_3$ | Formamide | 213 | 8.1 | 83.4 |
| CEx. 1 | AgNO$_3$ | Monoethanolamine | 209 | 8.0 | 72.3 |
| CEx. 2 | AgNO$_3$ | Monoethanolamine | 240 | 7.9 | 73.1 |
| CEx. 3 | AgNO$_3$ | Monoethanolamine | 235 | 8.0 | 73.3 |

EXAMPLE 3

The catalyst obtained by drying after washing with boiling water in Example 1 was impregnated with a mixed aqueous solution consisting of 1 ml of a 5.0% by weight aqueous solution of antimony lactate, 10 ml of a 2.2% by weight aqueous solution of thallium sulfate, and 300 ml of water in the air instead of the nitrogen atmosphere. Otherwise, the catalyst was prepared in the same way as in Example 1. By using the resulting catalyst, the same reaction as in Example 1 was performed. At a reaction temperature of 214° C., a conversion of 7.9% and a selectivity of 82.2% were obtained.

EXAMPLES 4 to 10

A catalyst was prepared in the same way as in Example 1 except that an aqueous solution of a compound of each of the metals shown in Table 2 was used instead of the mixed aqueous solution consisting of 1 ml of a 5.0% by weight aqueous solution of antimony lactate, 10 ml of a 2.2% by weight of thallium sulfate and 300 ml of water. By using the resulting catalyst, the same reaction as in Example 1 was performed. The results are shown in Table 2.

Table 2

| Example | Amount of promoter supported (gram-atoms per gram atom of silver) | | | | Amount of silver supported (wt. %) | Reaction temperature (°C.) | Results | |
|---|---|---|---|---|---|---|---|---|
| | Sb | Tl | K | Cs | | | Conversion (%) | Selectivity (%) |
| 4 | — | 0.002 | — | — | 4.5 | 214 | 7.9 | 82.1 |
| 5 | — | 0.002 | 0.001 | — | 4.5 | 220 | 8.0 | 82.3 |
| 6 | — | 0.002 | — | 0.001 | 4.5 | 225 | 8.0 | 81.5 |
| 7 | — | 0.0005 | — | 0.003 | 4.5 | 233 | 7.9 | 82.6 |
| 8 | — | 0.0005 | 0.002 | 0.003 | 4.5 | 236 | 7.9 | 82.9 |
| 9 | 0.0003 | 0.0005 | — | 0.003 | 4.5 | 228 | 8.0 | 83.2 |
| 10 | 0.0003 | 0.002 | 0.002 | — | 4.5 | 221 | 8.0 | 82.6 |

Note:
The above promoter components were supported by using the following solutions.
Sb: a 5.0% aqueous solution of antimony lactate;
Tl: a 2.2% by weight aqueous solution of thallium sulfate;
K: a 1.0% by weight aqueous solution of potassium nitrate;
Cs: a 2.5% by weight aqueous solution of cesium nitrate.

EXAMPLE 11

The procedure of Example 2 was repeated except that 37 g of silver nitrate, 300 g of ethylene glycol and 15 g of formamide were used instead of 75 g of silver nitrate, 270 g of monoethylene glycol and 30 g of formamide, and 7.5 ml of a 2.2% by weight aqueous solution of thallium sulfate was used instead of 1 ml of the 5.0% by weight aqueous solution of antimony lactate and 10 ml of the 2.2% by weight aqueous solution of thallium sulfate.

The resulting catalyst contained 2.5% by weight of metallic silver and thallium in an amount corresponding to about 0.003 gram atom per gram-atom of silver supported on it.

By using this catalyst, the same reaction as in Example 1 was carried out. After continuing the reaction for 240 hours, a conversion of 8.0% and a selectivity of 81.5% were obtained at a reaction temperature of 221° C.

What we claim is:

1. A process for preparing a silver-supported catalyst for the production of ethylene oxide by catalytic vapor phase oxidation of ethylene with molecular oxygen, the catalyst being composed of a porous inorganic carrier and fine particles of silver dispersed and deposited on its external surface and the internal wall surface of its pores, which comprises impregnating the porous inorganic carrier with a solution of a silver compound containing a reducing compound, said solution being
(A) a solution comprising
   (1) at least one alkanolamine selected from the group consisting of monoethanolamine, di-ethanolamine and triethanolamine,
   (2) at least one silver compound selected from the group consisting of silver nitrate, silver carbonate, silver acetate, silver lactate, silver succinate and silver glycolate and
   (3) at least one solvent selected from the group consisting of water, monoethylene glycol, di-ethylene glycol and triethylene glycol,
(B) a solution comprising
   (1) formaldehyde
   (2) silver nitrate and
   (3) water, or
(C) a solution comprising
   (1) at least one acid amide selected from the group consisting of formamide and acetamide,
   (2) silver nitrate and
   (3) at least one solvent selected from the group consisting of monoethylene glycol, di-ethylene glycol, triethylene glycol, tri-methylene glycol, monopropylene glycol, methyl cellosolve and methyl carbitol,
subjecting the impregnated product to a reducing treatment at a temperature of 50° to 200° C. to deposit metallic silver on the external surface of the carrier and the internal wall surface of its pores, washing the silver-supported carrier with water, a lower alcohol or both, drying it at a temperature of 90° to 100° C., until the silver-supported carrier is dried, impregnating the dried product with a solution containing a promoter, and then evaporating the liquid ingredients.

2. The process of claim 1 wherein the silver-supported carrier is washed with at least one solvent selected from the group consisting of water, methanol, ethanol, n-propanol and isopropanol.

3. The process of claim 1 wherein said promoter is at least one compound selected from the group consisting of alkali metal compounds, alkaline earth metal compounds and compounds of elements of Groups III, IV, V and VIII of the periodic table in at least one solvent selected from the group consisting of water, methanol, ethanol, n-propanol and isopropanol, and the liquid ingredients are evaporated at a temperature of 50° to 150° C.

4. The process of claim 1 wherein the promoter is a thallium compound, and its amount to be deposited is 0.00001 to 0.005 gram-atom as thallium per gram-atom of metallic silver.

5. The process of claim 1 wherein the promoter consists of a compound of thallium and a compound of antimony or tin, and its amount deposited on the catalyst is 0.00001 to 0.005 gram-atom as thallium and 0.00001 to 0.01 gram-atom as antimony or tin, per gram-atom of metallic silver.

6. The process of claim 1 wherein the promoter consists of a compound of thallium and a compound of cesium or potassium, and its amount to be deposited on the catalyst is 0.00001 to 0.005 gram-atom as thallium and 0.00001 to 0.008 gram-atom as cesium or 0.00001 to 0.01 gram-atom as potassium per-gram atom of metallic silver.

7. The process of claim 1 wherein the promoter consists of a compound of thallium, a compound of antimony or tin, and a compound of potassium or cesium, and its amount to be deposited on the catalyst is 0.00001 to 0.005 gram-atom as thallium, 0.00001 to 0.01 gram-atom as antimony or tin, and 0.00001 to 0.01 gram-atom as potassium or 0.00001 to 0.008 gram-atom as cesium per gram-atom of metallic silver.

8. The process of claim 1 wherein the porous inorganic carrier has a specific surface area of not more than 10 m$^2$/g, an apparent porosity of 40 to 60% by volume, and a pore volume of 0.1 to 0.5 cc/g.

9. A process for preparing a silver-supported catalyst for the production of ethylene oxide by catalytic vapor phase oxidation of ethylene with molecular oxygen, the catalyst being composed of a porous inorganic carrier and fine particles of silver dispersed and deposited on its external surface and the internal wall surface of its pores, which consists essentially of, in sequence, the steps of impregnating the porous inorganic carrier with a solution of a silver compound containing a reducing compound, said solution being (A) a solution comprising
  (1) at least one alkanolamine selected from the group consisting of monoethanolamine, di-ethanolamine and triethanolamine,
  (2) at least one silver compound selected from the group consisting of silver nitrate, silver carbonate, silver acetate, silver lactate, silver succinate and silver glycolate and
  (3) at least one solvent selected from the group consisting of water, monoethylene glycol, di-ethylene glycol and triethylene glycol, (B) a solution comprising
  (1) formaldehyde
  (2) silver nitrate and
  (3) water, or (C) a solution comprising
  (1) at least one acid amide selected from the group consisting of formamide and acetamide,
  (2) silver nitrate and
  (3) at least one solvent selected from the group consisting of monoethylene glycol, di-ethylene glycol, triethylene glycol, tri-methylene glycol, monopropylene glycol, methyl cellosolve and methyl carbitol, subjecting the impregnated product to a reducing treatment at a temperature of 50° to 200° C. to deposit metallic silver on the external surface of the carrier and the internal wall surface of its pores, washing the silver-supported carrier with water, a lower alcohol or both, drying it at a temperature of 50 to 150° C., until the silver-supported carrier is dried, impregnating the dried product with a solution containing a promoter, wherein the promoter is a compound of thallium, and the amount of the promoter deposited on the catalyst is 0.00001 to 0.005 gram-atom of thallium per gram-atom of metallic silver, and then evaporating the liquid ingredients.

* * * * *